United States Patent
Pagès et al.

(10) Patent No.: US 9,095,665 B2
(45) Date of Patent: Aug. 4, 2015

(54) THREE-LINE APHERESIS SYSTEM AND METHOD

(71) Applicant: Haemonetics Corporation, Braintree, MA (US)

(72) Inventors: Etienne Pagès, Cessy (FR); Michael Ragusa, Hingham, MA (US)

(73) Assignee: Haemonetics Corporation, Braintree, MA (US)

( * ) Notice: Subject to any disclaimer, the term of this patent is extended or adjusted under 35 U.S.C. 154(b) by 0 days.

(21) Appl. No.: 14/101,899

(22) Filed: Dec. 10, 2013

(65) Prior Publication Data

US 2014/0100506 A1    Apr. 10, 2014

Related U.S. Application Data

(62) Division of application No. 12/102,407, filed on Apr. 14, 2008, now Pat. No. 8,628,489.

(51) Int. Cl.
*A61M 1/36* (2006.01)
*A61M 1/38* (2006.01)
(Continued)

(52) U.S. Cl.
CPC ............. *A61M 1/367* (2013.01); *A61M 1/0209* (2013.01); *A61M 1/303* (2014.02); *A61M 1/3621* (2013.01);
(Continued)

(58) Field of Classification Search
CPC ... A61M 1/3696; A61M 1/305; A61M 1/307; A61M 1/30; A61M 2205/33; A61M 2205/3306; A61M 2205/3331; A61M 2205/3334; A61M 2205/3362; A61M 2202/00; A61M 2202/0021; A61M 2202/0413; A61M 2202/0415; A61M 2202/0429; A61M 2202/0439; A61M 1/3616; A61M 1/0209; A61M 1/3621; A61M 1/3693; A61M 1/387; A61M 1/367; A61M 1/38; A61M 2202/0071; A61M 1/303; A61M 1/304; A61M 1/3601; A61M 1/3603; A61M 1/3604
See application file for complete search history.

(56) References Cited

U.S. PATENT DOCUMENTS

| 1,025,059 A | 4/1912 | Hatton et al. |
| 1,611,725 A | 12/1926 | Degerth et al. |

(Continued)

FOREIGN PATENT DOCUMENTS

| EP | 0 128 683 A2 | 12/1984 | .............. A61M 1/03 |
| EP | 0 171 749 A1 | 2/1986 | .............. A61M 1/00 |

(Continued)

OTHER PUBLICATIONS

Alessandro Germano, *Authorized officer* European Patent Office, International Search Report and Written Opinion of the International Searching Authority—Application No. PCT/US2009/040166, dated Oct. 1, 2009 (15 pages).

(Continued)

*Primary Examiner* — Adam Marcetich

(74) *Attorney, Agent, or Firm* — Sunstein Kann Murphy & Timbers LLP

(57) ABSTRACT

A blood processing system for collecting and exchanging blood components includes a venous-access device for drawing whole blood from a subject and returning blood components to the subject. The system may include three lines connecting the venous access device to a blood component separation device and an anticoagulant source. A blood draw line fluidly connects to the venous-access device to the blood component separation device. An anticoagulant line introduces anticoagulant into the drawn whole blood. A return line, fluidly connected to the venous-access device and the blood component separation device, returns uncollected blood component to the subject. Each line may have a pump that controls flow through the line. The blood component separation device separates the drawn blood into a first blood component and a second blood component, and may be configured to send the first blood component to a first blood component bag.

15 Claims, 7 Drawing Sheets

(51) Int. Cl.
*A61M 1/02* (2006.01)
*A61M 1/30* (2006.01)

(52) U.S. Cl.
CPC ........... *A61M 1/3693* (2013.01); *A61M 1/3696* (2014.02); *A61M 1/387* (2013.01); *A61M 1/30* (2013.01); *A61M 1/304* (2014.02); *A61M 1/3601* (2014.02); *A61M 1/3603* (2014.02); *A61M 1/3604* (2014.02); *A61M 1/38* (2013.01); *A61M 2202/0071* (2013.01)

(56) References Cited

U.S. PATENT DOCUMENTS

| | | | |
|---|---|---|---|
| 2,087,778 A | 7/1937 | Nelin et al. | 210/64 |
| 2,661,150 A | 12/1953 | Abbott, Jr. | 233/27 |
| 2,750,107 A | 6/1956 | More | 233/2 |
| 2,792,172 A | 5/1957 | Tait | 233/2 |
| 3,096,283 A | 7/1963 | Hein | 233/20 |
| 3,145,713 A | 8/1964 | Latham, Jr. | 128/214 |
| 3,239,136 A | 3/1966 | Hein | 233/20 |
| 3,244,362 A | 4/1966 | Hein | 233/27 |
| 3,409,213 A | 11/1968 | Latham, Jr. | 233/21 |
| 3,456,875 A | 7/1969 | Hein | 233/24 |
| 3,489,145 A | 1/1970 | Judson et al. | 128/214 |
| 3,565,330 A | 2/1971 | Latham, Jr. | 233/21 |
| 3,655,058 A | 4/1972 | Novak | 210/360 |
| 3,737,096 A | 6/1973 | Jones et al. | 233/19 A |
| 3,774,840 A | 11/1973 | Boatright | 233/14 R |
| 3,987,961 A | 10/1976 | Sinn et al. | 233/27 |
| 4,007,871 A | 2/1977 | Jones et al. | 233/27 |
| 4,010,894 A | 3/1977 | Kellogg et al. | 233/27 |
| 4,014,497 A | 3/1977 | Spiewok et al. | 233/20 R |
| 4,040,965 A | 8/1977 | Kohlheb | 210/297 |
| 4,056,224 A | 11/1977 | Lolachi | 233/14 R |
| 4,082,217 A | 4/1978 | Westberg | 233/25 |
| 4,086,924 A | 5/1978 | Latham, Jr. | 128/214 R |
| 4,140,268 A | 2/1979 | Lacour | 233/1 |
| 4,142,670 A | 3/1979 | Ishimaru et al. | 233/20 R |
| 4,151,844 A | 5/1979 | Cullis et al. | 128/214 R |
| 4,197,847 A | 4/1980 | Djerassi | 128/214 R |
| 4,285,464 A | 8/1981 | Latham, Jr. | 233/26 |
| 4,300,717 A | 11/1981 | Latham, Jr. | 233/1 A |
| 4,303,193 A | 12/1981 | Latham, Jr. | 233/23 A |
| 4,321,921 A | 3/1982 | Laszczower | 128/276 |
| 4,387,848 A | 6/1983 | Kellogg et al. | 494/81 |
| 4,425,114 A | 1/1984 | Schoendorfer et al. | 604/7 |
| 4,430,072 A | 2/1984 | Kellogg et al. | 494/45 |
| 4,447,221 A | 5/1984 | Mulzet | 494/45 |
| 4,457,747 A | 7/1984 | Tu | 604/4 |
| 4,464,167 A | 8/1984 | Schoendorfer et al. | 604/6 |
| 4,466,888 A | 8/1984 | Verkaart | 210/232 |
| 4,482,342 A | 11/1984 | Lueptow et al. | 494/21 |
| 4,530,691 A | 7/1985 | Brown | 494/45 |
| 4,534,863 A | 8/1985 | Bacon et al. | 210/232 |
| 4,643,714 A | 2/1987 | Brose | 604/4 |
| 4,647,279 A | 3/1987 | Mulzet et al. | 494/45 |
| 4,680,025 A | 7/1987 | Kruger et al. | 604/6 |
| 4,684,361 A | 8/1987 | Feldman et al. | 494/41 |
| 4,692,136 A | 9/1987 | Feldman et al. | 494/38 |
| 4,708,712 A | 11/1987 | Mulzet | 494/45 |
| 4,734,089 A | 3/1988 | Cullis | 494/27 |
| 4,740,202 A | 4/1988 | Stacey et al. | 604/119 |
| 4,740,313 A | 4/1988 | Schoendorfer et al. | 210/651 |
| 4,755,300 A | 7/1988 | Fischel et al. | 210/650 |
| 4,767,396 A | 8/1988 | Powers | 494/60 |
| 4,795,419 A | 1/1989 | Yawn et al. | 494/84 |
| 4,795,448 A | 1/1989 | Stacey et al. | 604/319 |
| 4,806,247 A | 2/1989 | Schoendorfer et al. | 210/321.18 |
| 4,806,252 A | 2/1989 | Brown et al. | 210/744 |
| 4,808,307 A | 2/1989 | Fischel et al. | 210/321.68 |
| 4,850,995 A | 7/1989 | Tie et al. | 604/6 |
| 4,869,812 A | 9/1989 | Schoendorfer et al. | 210/321.63 |
| 4,871,462 A | 10/1989 | Fischel et al. | 210/651 |
| 4,876,013 A | 10/1989 | Shmidt et al. | 210/650 |
| 4,889,524 A | 12/1989 | Fell et al. | 494/12 |
| 4,911,833 A | 3/1990 | Schoendorfer et al. | 210/167 |
| 4,934,995 A | 6/1990 | Cullis | 494/45 |
| 4,940,543 A | 7/1990 | Brown et al. | 210/369 |
| 4,943,273 A | 7/1990 | Pages | 494/41 |
| 4,968,295 A | 11/1990 | Neumann | 604/6 |
| 4,983,156 A | 1/1991 | Knelson | 494/28 |
| 4,983,158 A | 1/1991 | Headley | 494/41 |
| 4,985,153 A | 1/1991 | Kuroda et al. | 210/782 |
| 4,994,188 A | 2/1991 | Prince | 210/636 |
| 5,039,401 A | 8/1991 | Columbus et al. | 210/117 |
| 5,045,048 A | 9/1991 | Kaleskas et al. | 494/41 |
| 5,098,372 A | 3/1992 | Jonsson | 604/5 |
| 5,098,373 A * | 3/1992 | Polaschegg | 604/6.05 |
| 5,100,372 A | 3/1992 | Headley | 494/41 |
| 5,100,564 A | 3/1992 | Pall et al. | 210/782 |
| 5,112,298 A | 5/1992 | Prince et al. | 604/6 |
| 5,114,396 A | 5/1992 | Unger et al. | 494/37 |
| 5,135,667 A | 8/1992 | Schoendorfer | 210/782 |
| 5,141,486 A | 8/1992 | Antwiler | 494/37 |
| 5,147,290 A | 9/1992 | Jonsson | 604/5 |
| 5,154,716 A | 10/1992 | Bauman et al. | 604/410 |
| 5,174,894 A | 12/1992 | Ohsawa et al. | 210/86 |
| 5,194,145 A | 3/1993 | Schoendorfer | 210/90 |
| 5,217,426 A | 6/1993 | Bacehowski et al. | 494/45 |
| 5,217,427 A | 6/1993 | Cullis | 494/45 |
| 5,234,403 A | 8/1993 | Yoda et al. | 604/4 |
| 5,254,248 A | 10/1993 | Nakamura | 210/321.67 |
| 5,273,517 A | 12/1993 | Barone et al. | 494/37 |
| 5,277,701 A | 1/1994 | Christie et al. | 604/4 |
| 5,298,016 A | 3/1994 | Gordon | 604/4 |
| 5,298,171 A | 3/1994 | Biesel | 210/739 |
| 5,300,060 A | 4/1994 | Nelson | 604/410 |
| 5,316,540 A | 5/1994 | McMannis et al. | 494/37 |
| 5,318,512 A | 6/1994 | Neumann | 604/6 |
| 5,348,533 A | 9/1994 | Papillon et al. | 604/4 |
| 5,368,542 A | 11/1994 | McMannis et al. | 494/45 |
| 5,386,734 A | 2/1995 | Pusinelli | 73/863.21 |
| 5,387,174 A | 2/1995 | Rochat | 494/10 |
| 5,387,187 A * | 2/1995 | Fell et al. | 604/6.02 |
| 5,403,272 A | 4/1995 | Deniega et al. | 604/4 |
| 5,405,308 A | 4/1995 | Headley et al. | 494/67 |
| 5,417,650 A | 5/1995 | Gordon | 604/4 |
| 5,431,814 A | 7/1995 | Jorgensen | 210/399 |
| 5,437,598 A | 8/1995 | Antwiler | 494/1 |
| 5,437,624 A | 8/1995 | Langley | 604/4 |
| 5,462,667 A | 10/1995 | Wollinsky et al. | 210/645 |
| 5,470,483 A | 11/1995 | Bene et al. | 210/741 |
| 5,484,396 A | 1/1996 | Naficy | 604/4 |
| 5,494,592 A * | 2/1996 | Latham et al. | 210/805 |
| 3,244,363 A | 4/1996 | Hein | 233/28 |
| 5,505,685 A | 4/1996 | Antwiler | 494/37 |
| 5,514,070 A | 5/1996 | Pages | 494/41 |
| 5,543,062 A | 8/1996 | Nishimura | 210/782 |
| 5,551,941 A | 9/1996 | Howell | 494/16 |
| 5,585,007 A | 12/1996 | Antanavich et al. | 210/782 |
| 5,607,579 A | 3/1997 | Latham, Jr. et al. | 210/195.1 |
| 5,649,903 A | 7/1997 | Deniega et al. | 604/4 |
| 5,651,766 A | 7/1997 | Kingsley et al. | 604/6 |
| 5,656,163 A | 8/1997 | Brown | 210/360.1 |
| 5,712,798 A | 1/1998 | Langley et al. | 364/500 |
| 5,728,060 A | 3/1998 | Kingsley et al. | 604/4 |
| 5,733,253 A | 3/1998 | Headley et al. | 604/4 |
| 5,733,446 A | 3/1998 | Holm | 210/206 |
| 5,733,545 A | 3/1998 | Hood, III | 424/93.72 |
| 5,738,792 A | 4/1998 | Schoendorfer | 210/651 |
| 5,762,791 A | 6/1998 | Deniega et al. | 210/321.67 |
| 5,779,660 A | 7/1998 | Kingsley et al. | 604/6 |
| 5,783,085 A | 7/1998 | Fischel | 210/651 |
| 5,792,351 A | 8/1998 | Wehrle et al. | 210/321.67 |
| 5,849,203 A | 12/1998 | Brown et al. | 210/782 |
| 5,882,289 A | 3/1999 | Sakota et al. | 494/41 |
| 5,906,589 A | 5/1999 | Gordon et al. | 604/65 |
| 5,919,125 A | 7/1999 | Berch | 494/67 |
| 5,964,724 A | 10/1999 | Rivera et al. | 604/4 |
| 5,980,760 A | 11/1999 | Min et al. | 210/782 |
| 6,007,725 A | 12/1999 | Brown | 210/739 |
| 6,059,979 A | 5/2000 | Brown | 210/739 |
| 6,207,063 B1 | 3/2001 | Brown | 210/739 |
| 6,234,989 B1 | 5/2001 | Brierton et al. | 604/5.01 |

(56) References Cited

U.S. PATENT DOCUMENTS

| | | | |
|---|---|---|---|
| 6,296,602 B1 | 10/2001 | Headley | 494/37 |
| 6,464,624 B2 | 10/2002 | Pages | 494/36 |
| 6,558,307 B2 | 5/2003 | Headley | 494/37 |
| 6,652,476 B2 | 11/2003 | Langley et al. | 604/6.01 |
| 6,743,192 B1 | 6/2004 | Sakota et al. | 604/6.01 |
| 7,115,205 B2 | 10/2006 | Robinson et al. | 210/789 |
| 7,186,231 B2 | 3/2007 | Takagi et al. | 604/6.01 |
| 7,270,645 B2 | 9/2007 | Langley et al. | 604/6.01 |
| 7,704,454 B1 | 4/2010 | Langley et al. | 422/44 |
| 8,702,637 B2 * | 4/2014 | Pages et al. | 604/6.01 |
| 2001/0027156 A1 | 10/2001 | Egozy et al. | 494/37 |
| 2002/0032398 A1 * | 3/2002 | Steele et al. | 604/6.01 |
| 2002/0043492 A1 | 4/2002 | Bischof | 210/258 |
| 2003/0203802 A1 * | 10/2003 | Westberg et al. | 494/43 |
| 2004/0096814 A1 * | 5/2004 | Langley et al. | 435/2 |
| 2004/0199098 A1 * | 10/2004 | Pierce et al. | 604/4.01 |
| 2005/0000868 A1 * | 1/2005 | Weigel et al. | 210/90 |
| 2005/0209522 A1 * | 9/2005 | Tadokoro et al. | 600/508 |
| 2006/0058167 A1 | 3/2006 | Ragusa et al. | 494/5 |
| 2006/0155236 A1 * | 7/2006 | Gara et al. | 604/4.01 |

FOREIGN PATENT DOCUMENTS

| | | | | |
|---|---|---|---|---|
| EP | 0 208 061 A1 | 1/1987 | | A61M 1/34 |
| EP | 0 257 755 A1 | 3/1988 | | A61M 1/36 |
| EP | 0 578 086 A1 | 1/1994 | | A61M 1/36 |
| EP | 0 619 145 A2 | 10/1994 | | B04B 9/12 |
| EP | 0 664 159 A1 | 7/1995 | | B04B 5/04 |
| EP | 0 799 645 A1 | 10/1997 | | B04B 5/04 |
| EP | 0 885 619 A1 | 12/1998 | | A61M 1/36 |
| EP | 1 057 534 A1 | 12/2000 | | B04B 5/04 |
| EP | 1 374 927 A1 | 1/2004 | | A61M 1/02 |
| FR | 2 258 898 A1 | 8/1975 | | |
| GB | 2 047 110 A | 11/1980 | | A61M 1/03 |
| JP | 59-006952 A | 1/1984 | | B04B 5/00 |
| JP | 59-069166 A | 4/1984 | | B04B 11/00 |
| JP | 07-075746 A | 3/1995 | | B04B 1/02 |
| JP | 08-131539 A | 5/1996 | | A61M 1/02 |
| JP | 09-192215 A | 7/1997 | | A61M 1/02 |
| JP | 11-504836 | 5/1999 | | A61M 1/02 |
| JP | 2002-291872 A | 10/2002 | | A61M 1/02 |
| JP | 2003-516175 | 5/2003 | | A61M 1/02 |
| JP | 2005-110748 | 4/2005 | | A61M 1/02 |
| JP | 2008-506424 A | 3/2008 | | A61M 1/02 |
| SU | 660718 A1 | 5/1979 | | B04B 5/00 |
| SU | 762982 | 9/1980 | | B04B 5/00 |
| SU | 1146098 A | 3/1985 | | B04B 5/00 |
| WO | WO 85/02561 A1 | 6/1985 | | B04B 1/10 |
| WO | WO 90/00059 A1 | 1/1990 | | A61K 35/14 |
| WO | WO 90/07383 A1 | 7/1990 | | B04B 7/08 |
| WO | WO 94/06535 A1 | 3/1994 | | B01D 33/00 |
| WO | WO 96/11747 A2 | 4/1996 | | B04B 5/04 |
| WO | WO 96/33023 A1 | 10/1996 | | B04B 5/04 |
| WO | WO 96/40322 | 12/1996 | | A61M 1/36 |
| WO | WO 01/28621 | 4/2001 | | A61M 37/00 |
| WO | WO 2007/041716 A1 | 4/2007 | | A61M 1/36 |

OTHER PUBLICATIONS

The State Intellectual Property Office of the People's Republic of China, First Official Action—Application No. 200980120814.6, dated Jan. 4, 2013 (6 pages).

The State Intellectual Property Office of the People's Republic of China, First Official Action (Notification of the First Office Action)—Application No. 200980120814.6, dated Jan. 4, 2013 (6 pages) [English Translation].

Hu, Yating, The State Intellectual Property Office of the People's Republic of China, Second Official Action—Application No. 200980120814.6, dated Nov. 18, 2013 (7 pages).

Hu, Yating, The State Intellectual Property Office of the People's Republic of China, Second Official Action (Notification of the Second Office Action)—Application No. 200980120814.6, dated Nov. 18, 2013 (8 pages) [English Translation].

Japanese Patent Office, First Official Action—Application No. 2011-504,195, dated May 28, 2013 (3 pages).

Japanese Patent Office, First Official Action—Application No. 2011-504,195, dated May 28, 2013 (3 pages) [English Translation].

Japanese Patent Office, Final Official Action—Application No. 2011-504,195, dated Oct. 2, 2013 (2 pages).

Japanese Patent Office, Final Official Action (Final Decision for Rejection)—Application No. 2011-504,195, dated Oct. 2, 2013 (2 pages) [English Translation].

Japanese Patent Office, First Official Action—Application No. 2014-021910, dated Dec. 19, 2014 (2 pages).

Japanese Patent Office, First Official Action—Application No. 2014-021910, dated Dec. 19, 2014 (2 pages) [English Translation].

* cited by examiner

THREE-LINE APHERESIS SYSTEM AND METHOD

PRIORITY

This application is a divisional of co-pending U.S. patent application Ser. No. 12/102,407, entitled "Three-Line Apheresis System and Method," filed Apr. 14, 2008, and naming Etienne Pages and Michael Ragusa as inventors, the disclosure of which is incorporated herein, in its entirety, by reference.

TECHNICAL FIELD

The present invention relates systems and methods for blood processing, and particularly to a three line apheresis system and methods of using the same.

BACKGROUND ART

Apheresis is a procedure in which an individual blood component can be separated and collected from whole blood temporarily withdrawn from a subject. Typically, whole blood is withdrawn through a needle inserted into the subjects arm and into a cell separator, such as a centrifugal bowl. Once the whole blood is separated into its various components (e.g., plasma, red blood cells, white blood cells, and platelets), one or more of the components can be removed from the centrifugal bowl. The remaining components are returned to the subject with optional fluid compensation to make up for the volume of the removed component.

One concern with apheresis systems is the amount of extra corporeal volume (ECV), or the amount of whole blood that is outside of the body during the procedure. For the safety of the donor subject and to improve the donor subject's tolerance to the procedure, the extra corporeal volume should be minimized. The limits on the ECV have created a variety of apheresis systems and separation device designs. For example, current apheresis systems typically employ either a continuous flow separation device or discontinuous flow separation device. Continuous flow separation devices do not typically accumulate separated components within the device during separation (although a container may be added external to the separation device). Conversely, blood components typically accumulate within a discontinuous separation device and are later removed or extracted from the separation device.

Another significant difference between continuous and discontinuous separation devices is the number of access ports that each have. In particular, continuous flow separation devices typically have at least 3 access ports (1 input port for the anticoagulated whole blood, and 2 component output ports), whereas discontinuous separation devices only have two ports (an inlet and an outlet).

Apheresis systems utilizing discontinuous separation devices (e.g., a two port centrifuge bowl) draw whole blood from the donor or patient through a conduit into the centrifuge bowl, where component separation takes place. When there is sufficient volume in the bowl, the drawing of fresh blood is stopped, and the unwanted components are returned to the donor or patient through the same conduit intermittently, which creates lag times and increases the overall procedure time. When the return has been completed, whole blood is again drawn from the donor or patient, and a second cycle begins. This batch process continues until the desired amount of component has been collected.

SUMMARY OF THE INVENTION

In accordance with embodiments of the present invention, a blood processing system may collect, remove, and exchange blood components. The blood processing system may be a discontinuous system and may include a venous-access device for drawing whole blood from a subject and returning blood components to the subject, and a blood component separation device. The blood component separation device separates the drawn blood into at least a first blood component and a second blood component, and may be configured to send the first blood component to a first blood component bag. The blood component separation device may also have an outlet and may alternate between discharging the first blood component and the second blood component through the outlet. The blood processing system may also have a plurality of lines including, but not limited to, a blood draw line, an anticoagulant line, and a return line. A line specific pump can control the flow through each of these lines.

The blood draw line may be fluidly connected to the venous-access device and configured to transport the drawn whole blood to the blood component separation device. A blood draw pump may control the flow through the blood draw line. The anticoagulant line may be connected to an anticoagulant source, and may introduce anticoagulant into the drawn whole blood, for example, near the venous access device. An anticoagulant pump may control the flow through the anticoagulant line. The return line may fluidly connect the venous-access device and the blood component separation device, and may be used to return the second blood component or compensation fluid to the subject. A return pump may control the flow through the return line. In some embodiments, the return line fluidly connects to the venous-access device at a point between the blood draw pump and the venous-access device.

In accordance with other embodiments, the blood component separation device is a centrifuge bowl, and may separate the drawn blood into a third blood component in addition to the first blood component and the second blood component. The third blood component may be returned to the subject in addition to the second blood component via the return line. The first blood component may be plasma, the second blood component may be red blood cells, and the third blood component may be platelets or other blood cell. Alternatively, the first blood component may be platelets and the third blood component may be plasma.

In accordance with further embodiments, a surge elutriation step may be used to extract the plasma from the bowl using saline solution or other compensation fluid. Additionally, the system may include a valve located on the return line between the blood component separation device and the venous-access device. The valve stops the flow within the return line. During surge elutriation, the blood component separation device may send the first blood component to the first blood component bag. The system may also have a plasma reservoir, located in the return line that holds the plasma.

In accordance with still further embodiments of the present invention, a method of collecting and exchanging blood components is used. The method includes inserting a venous-access device into a subject, and withdrawing blood from the subject. The venous-access device may be connected to a draw line, an anticoagulation line, and a return line. The method withdraws the blood from the subject through the draw line, which is connected to a blood component separation device. A draw line pump controls the flow through the draw line. The method may also introduce anticoagulant into the withdrawn blood through the anticoagulant line. An anticoagulant line pump controls the flow through the anticoagulant line. The amount of blood withdrawn from the subject does not necessarily need to fill the blood component separation device.

Once the withdrawn blood is within the blood component separation device, the method separates the withdrawn blood into a first blood component and a second blood component, and extracts the first blood component from the blood component separation device. The method may then return the second blood component to the subject through the return line that fluidly connects to the venous-access device at a point between the draw line pump and the venous-access device. A return line pump controls the flow through the return line. The blood component separation device may be a centrifuge bowl.

In accordance with other embodiments, the method may also pause the withdrawal of blood while returning the second component to the patient, and repeating some or all of the steps until a target plasma volume is extracted. Additionally, the method may also monitor a pressure within the return line, and adjust the flow of fluid within the return line based on the monitored pressure to maintain the pressure within a desired pressure range. The method may also return a volume of compensation fluid to the subject after blood is drawn from the subject to compensate for the volume of withdrawn blood.

In accordance with still other embodiments, a blood processing system for collecting and exchanging blood components may include a venous-access device for drawing whole blood from a subject and returning blood components to the subject. The system may also have a two-port blood component separation device that separates the drawn blood into a first blood component and a second blood component and sends the first blood component to a first blood component bag. The blood processing system may also have a plurality of lines including, but not limited to, a blood draw line, an anticoagulant line, and a return line. A line specific pump can control the flow through each of these lines.

The blood draw line may be fluidly connected to the venous-access device and configured to transport the drawn whole blood to the blood component separation device. A blood draw pump may control the flow through the blood draw line. The anticoagulant line may be connected to an anticoagulant source, and may introduce anticoagulant into the drawn whole blood, for example, near the venous access device. An anticoagulant pump may control the flow through the anticoagulant line. The return line may fluidly connect the venous-access device and the blood component separation device, and may be used to return the second blood component or compensation fluid to the subject. A return pump may control the flow through the return line. In some embodiments, the return line fluidly connects to the venous-access device at a point between the blood draw pump and the venous-access device. The two-port blood component separation device may be a centrifuge bowl. The first blood component may be plasma and the second blood component may be red blood cells. Alternatively, the first blood component may be platelets and the second blood component may be plasma.

BRIEF DESCRIPTION OF THE DRAWINGS

The foregoing features of the invention will be more readily understood by reference to the following detailed description, taken with reference to the accompanying drawings, in which.

DETAILED DESCRIPTION OF SPECIFIC EMBODIMENTS

Embodiments of the present invention provide a system and method for performing blood apheresis procedures. Specific embodiments offer three-line, single access blood apheresis systems that provide for a decreased overall procedure time, with only limited "dead times," decreased extra corporeal volume, processing of all drawn blood and minimum exposure of drawn blood to processed returned blood. The method and system may use dedicated lines for withdrawing blood from a subject, introducing anti-coagulant into the drawn blood, and returning unused or processed blood components to the subject. Details of the illustrative embodiments are discussed below.

Figure 1:
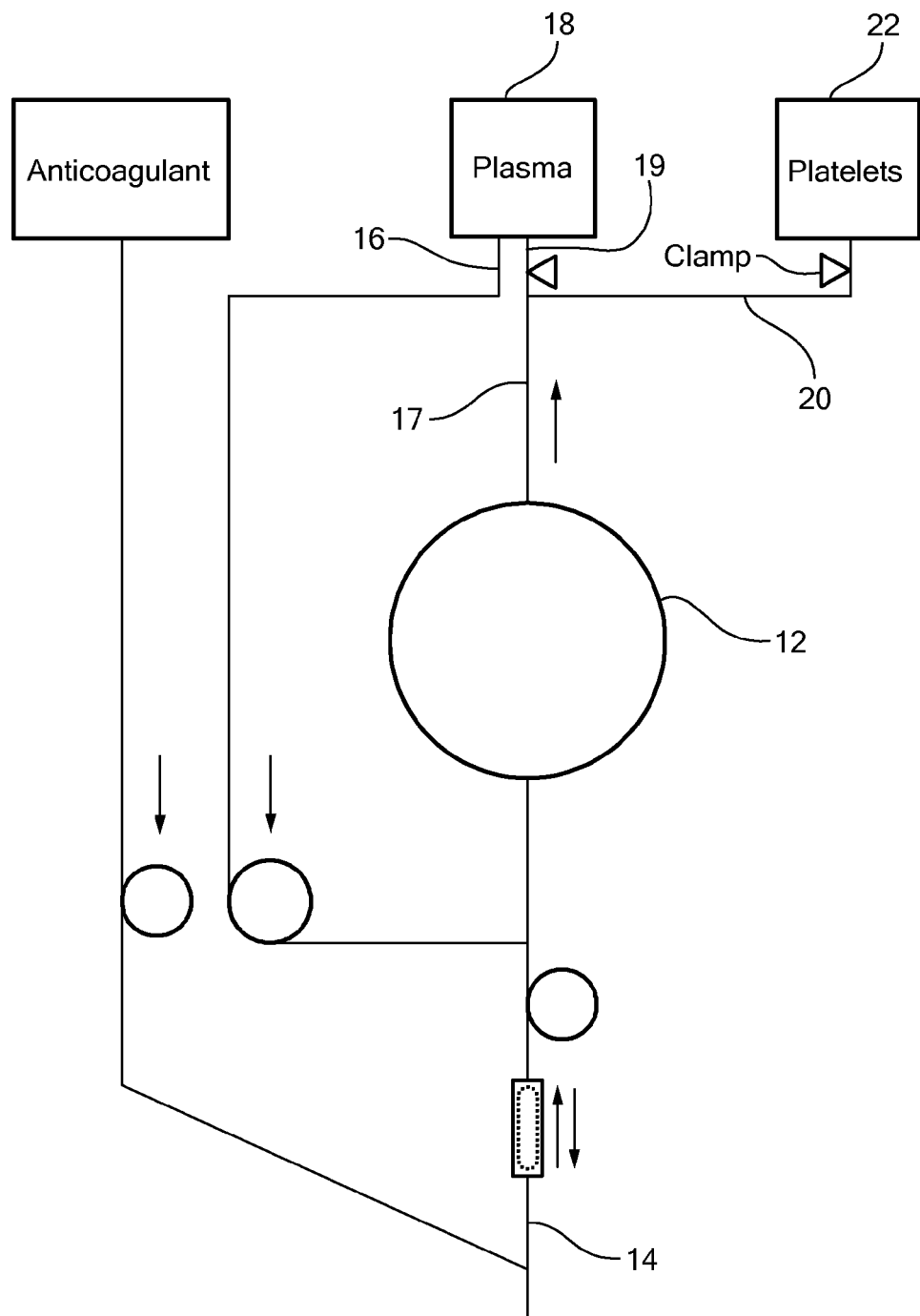
FIG. 1 schematically shows the general configuration of a prior art two-port, single access blood processing system.

As shown in FIG. 1, and as mentioned above, prior art systems 10 utilizing two-port separation devices (e.g., centrifuge bowl 12) draw whole blood from the donor or patient through a conduit 14 into the centrifuge bowl 12, where component separation takes place. When there is sufficient volume in the bowl 12, the system 10 stops drawing whole blood, desired components are collected (e.g., plasma via line 19 and bag 18 and/or platelets via line 20 and bag 22), and the unwanted components are returned to the donor or patient through the same conduit 14 intermittently, which creates lag times and increases the overall procedure time. When the return step is complete, whole blood is again drawn from the donor or patient, and a second cycle begins. This batch process continues until the desired amount of component has been collected. It is important to note that, because there are only two-ports on the centrifuge bowl 12, the extracted components share a length of conduit 17 before breaking off into their respective conduits (e.g., the plasma bag line 19 and the platelet bag line 20).

Figure 2:
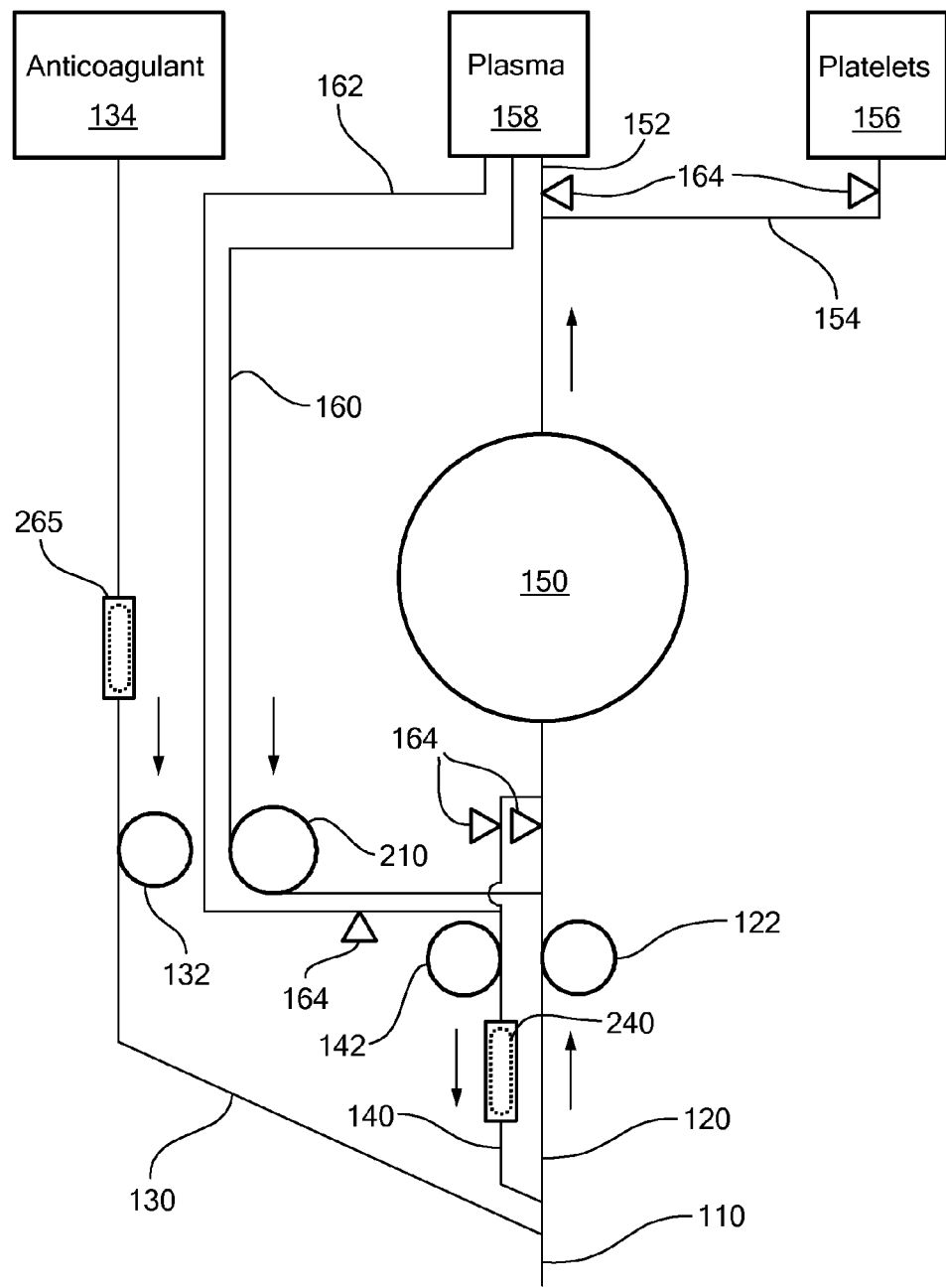
FIG. 2 schematically shows the general configuration of a three-line, single access system in accordance with embodiments of the present invention.

In contrast, as shown in FIG. 2, embodiments of the present invention withdraw whole blood from a subject and return un-extracted and/or unwanted components to the subject via dedicated lines. In particular, the blood processing system 100 withdraws whole blood from the subject through a venous-access device 110 that may be inserted into the subjects arm. The venous-access device 110 may have three-lines extending from it. The first line, the blood draw line 120, fluidly connects the venous-access device 110 to a blood component separation device 150. Therefore, as whole blood withdrawn from the subject, the blood passes through the venous-access device 110 to the blood component separation device via the draw line 120. A draw pump 122, located on the draw-line, controls the direction, rate, and duration of the withdraw flow through the draw line 120.

As the whole blood is being withdrawn from the subject, anticoagulant can be added to the whole blood to prevent the blood from coagulating within the lines or within the blood component separation device 150. To that end, the system may include an anticoagulant line 130 fluidly connected to an anticoagulant source 134 (e.g., a bag of anticoagulant) at one end, and the venous-access device 110 (or the draw line 120) at the other end. An anti-coagulant pump 132, through which the anticoagulant line 130 passes, may control the flow through the anti-coagulant line 130 and the amount of anti-coagulant introduced into the whole blood. In some embodiments, the anticoagulant pump 132 operates proportionately to the draw pump 122 to ensure that the proper amount of anticoagulant is added to the whole blood. Although the anticoagulant can be added to the whole blood at any point, it is preferred that the anticoagulant be introduced into the whole blood as close as possible to the venous-access device 110. It is important to note that any of the lines/conduits can include a clamp valve 164 to stop the flow within the line.

Once a desired amount of anti-coagulated whole blood is withdrawn from the subject and contained within the blood component separation device 150, the blood component separation device separates the whole blood into several blood components. For example, the blood component separation device may separate the whole blood into a first, second, third blood component, and, perhaps, a fourth blood component. More specifically, the blood component separation device 150 can separate the whole blood into plasma, platelets, red blood cells, and, perhaps, white blood cells.

As discussed in greater detail below, some embodiments of the blood processing system 100 can include a transfer pump 210 and a dilution/extraction line 160 connected to the plasma bag 158. The transfer pump 210 and dilution/extraction line 160 can be used for a variety of purposes including dilution of the anticoagulated drawn blood being introduced into the blood component separation device. For example, if the user wishes the drawn blood to have a higher plasma content, the system can dilute the withdrawn blood by turning on the transfer pump and introducing plasma from the plasma bag 158 into the withdrawn blood within the draw line 120. Additionally or alternatively, the transfer pump may be used during surge elutriation (discussed in greater detail below) to introduce plasma from the plasma bag 158 into the blood component separation device 150 to extract the platelets (or other blood component).

Although a variety of blood component separation devices 150 can be used to separate the whole blood into blood components, some embodiments of the present invention use a standard Latham type centrifuge, as described in U.S. Pat. No. 3,145,713, which is hereby incorporated by reference. However, other embodiments of the present invention can use other blood component separation devices 150, such as, but not limited to, integral blow-molded centrifuge bowls, as described in U.S. Pat. Nos. 4,983,156 and 4,943,273, which are hereby incorporated by reference.

Figure 4:
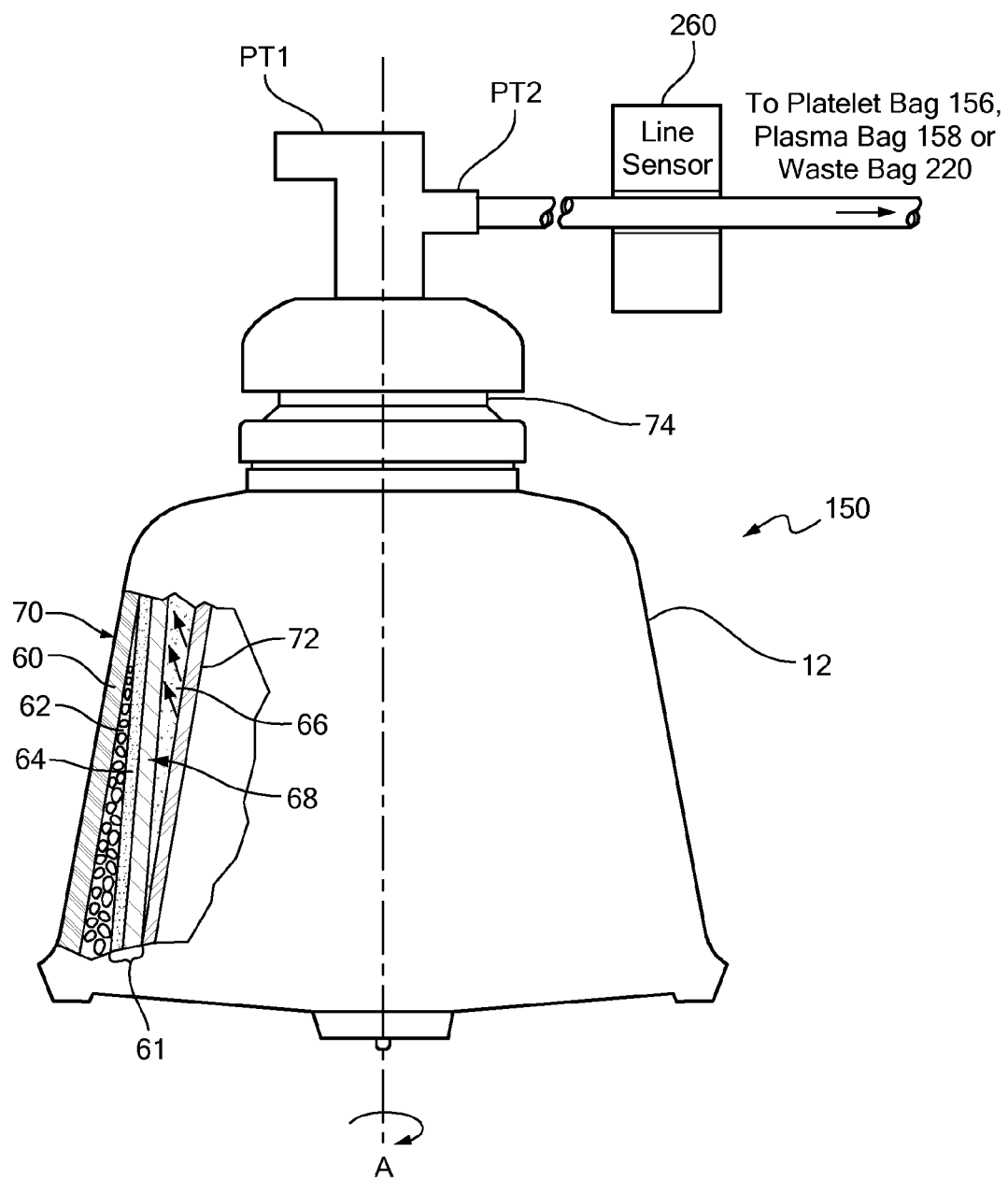
FIG. 4 schematically shows a side view of a two-port centrifuge bowl for use with the machine of FIG. 1, in accordance with one embodiment of the invention.

As shown in FIG. 4, when a Latham centrifuge 11 is used, the blood component separation device 150 includes a rotatable bowl 12 and stationary input and output ports PT1 and PT2 fluidly coupled to the bowl interior by a rotary seal 74. The draw line 120 fluidly connects the venous access devices 110 (e.g., a phlebotomy needle) and the input port PT1. In some embodiments, the venous access device 110 may be replaced with a whole blood bag (not shown) in case the whole blood is to be first pooled and then supplied. In such embodiments, the draw line 120 will fluidly connect the whole blood bag with the input port PT1.

As mentioned above, the blood component separation device 150 separates the whole blood into its constituent components. In particular, as the bowl 12 rotates, centrifugal forces separate the anticoagulated whole blood admitted into the bottom of the bowl into red blood cells (RBC), white blood cells (WBC), platelets and plasma. The number of rotations of the bowl 12 can be selected, for example, within a range of 4,000 to 6,000 rpm, and is typically 4,800 rpm. The blood is separated into different fractions in accordance with the component densities. The higher density component, i.e., RBC 60, is forced to the outer wall 70 of the bowl 12 while the lower density plasma 66 lies nearer the core 72. A buffy coat 61 is formed between the plasma 66 and the RBC 60. The buffy coat 61 is made up of an inner layer of platelets 64, a transitional layer 68 of platelets and WBC and an outer layer of WBC 62. The plasma 66 is the component closest to the outlet port from the separation region and is the first fluid component displaced from the bowl 12 via the outlet port PT2 as additional anticoagulated whole blood enters the bowl 12 through the inlet port PT1.

Figure 3:
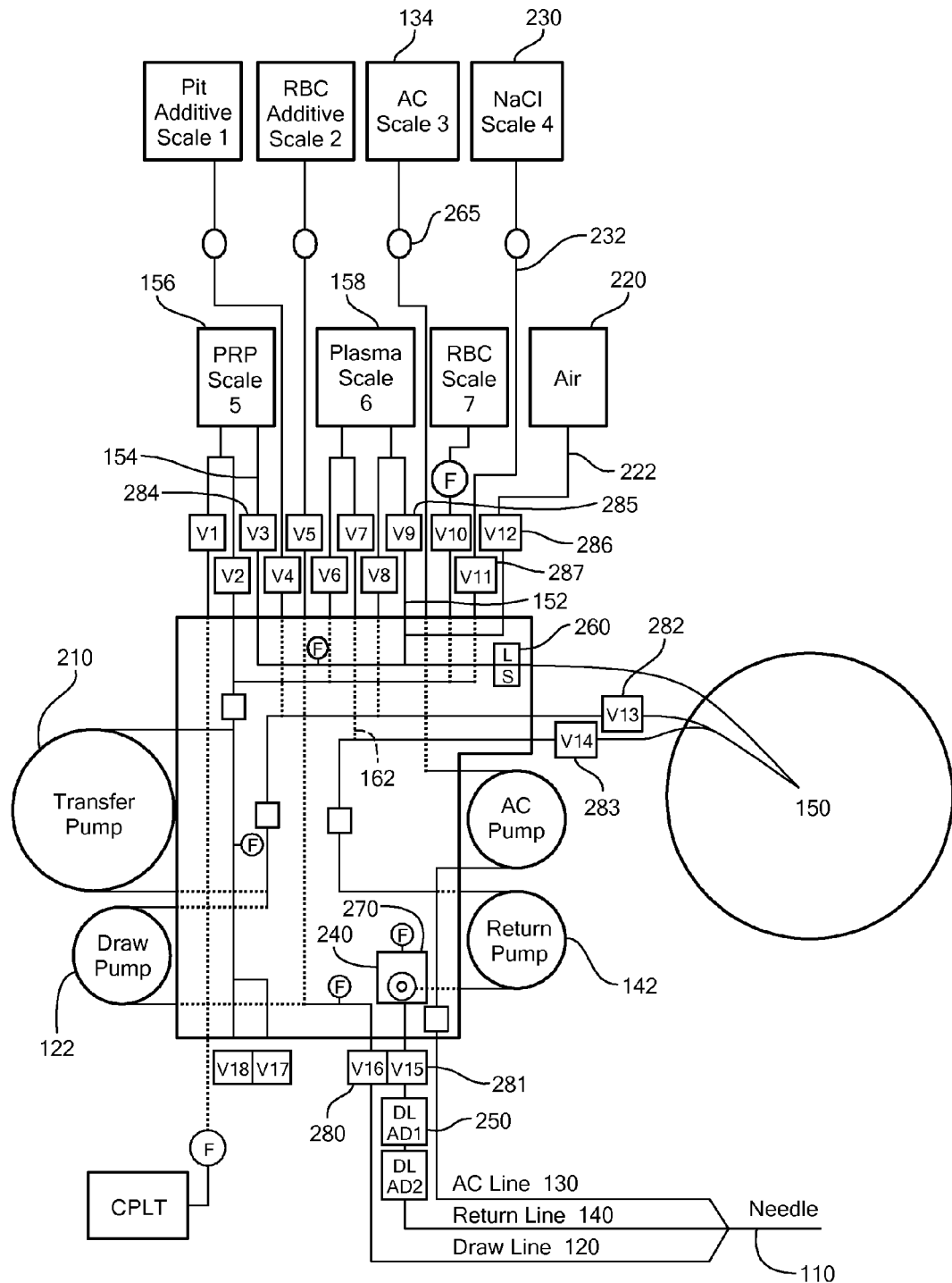
FIG. 3 schematically shows a more detailed configuration of a three-line, single access system in accordance with embodiments of the present invention.

Once the blood component separation device 150 has separated the blood into the various components, one or more of the components can be removed from the blood component separation device 150. For instance, the plasma may be removed to a plasma bag 158 through line 152 (FIG. 2 and FIG. 3) or a waste bag 220 through line 222 (FIG. 3). Alternatively, the plasma may be removed to a plasma reservoir (not shown) located on the return line 140. The removed plasma (or a compensation fluid) may be later reintroduced into the blood component separation device 150 at an increasing rate to extract and send the platelets to a platelet bag 156 via line 154. This process is known as surge elutriation. Once the desired components are removed from the blood component separation device, the system can return the remaining components to the subject. The system may return the components to the subject via a dedicated return line 140. The return line 140 fluidly connects the blood component separation device 150 and the venous-access device 110. In preferred embodiments, the return line 140 fluidly connects to the venous-access device 110 at a point between the blood draw pump 122 and the venous-access device 110. Like the anticoagulant line 130 and the draw line 120, the return line 140 also has a dedicated pump 142. The return pump 142 controls the direction, rate, and duration of the fluid flow within the return line 142. In some embodiments, the system may also have a plasma return line 162 that fluidly connects with the return line 140 upstream of the return pump 142. The plasma return line 162 allows the system 100 to return plasma contained within the plasma bag 158 to the subject. The plasma return line 162 may utilize the return pump 142 to return the plasma to the subject.

In accordance with some embodiments, the system 100 may draw the whole blood, separate it into components, and extract the blood components from a blood component separation device in a discontinuous, batch-like process. For example, the system 100 may draw whole blood from the subject until a specific volume is within the blood component separation device 150. The system 100 may then separate the blood contained within the blood component separation device 150, collect the desired blood component, and return the remaining blood components to the subject. The system 100 may then draw more whole blood from the subject and repeat the process, for example, until a predetermined amount of blood component is collected. In some embodiments, particularly those having only a single outlet on the blood component separation device 150, the blood component separation device 150 can alternate between discharging the first blood component and the second blood component through the same outlet (e.g., PT2 shown in FIG. 4). For example, the blood component separation device 150 may first discharge plasma to the plasma bag 158 and then return the remaining blood components to the subject through the same outlet.

As shown in FIG. 3, in addition to the above described system components, the system may also include a number of valves, filters, pressure monitors and sensors that help facilitate the operation of the overall system. In particular, each of the above described lines may contain a filter within the line. For example, the return line 140 may contain a blood filter 240 through which the returning blood components must pass. Additionally, the anticoagulant line 130 may include a bacteria filter 265 that prevents any bacteria in the anticoagulant source 134 from entering the system. Although the draw line 120 may have a blood filter (not shown), it should be noted that, unlike traditional systems that utilize the same line for both withdrawing blood from the subject and returning the unused components, embodiments of the present invention do not need a filter on the draw line 120. In particular, this is because the return line contains a filter that removes any contamination that may be present in the fluids returning to the body. By removing the filter on the draw line, the draw step can be faster, more efficient, and the draw pump does not need to work as hard. Alternatively, the system may use a smaller capacity pump. Additionally, avoiding filtration on the draw line 120 and not using the same line to draw whole blood and return blood component prevents potential microaggregates from being displaced back and forth from the filter to the separation device 150.

As discussed in greater detail below, the system can have a plurality of valves located through-out the system to control the flow of fluid within the system. For example, the return and draw lines may contain a valve (e.g., valves 281 and 280, respectively) that allow flow through the lines when open and prevent flow when closed. Additionally, each of the lines 152, 154, 222, 232 leading to the storage and waste bags 156, 158, and 220, and the compensation fluid source 230 may have similar valves (e.g., valves 285, 284, 286, and 287, respectively). Additionally, the inlet to the blood component separation device 150 may have valves 282 and 283 that either allow or prevent flow to or from the blood component separation device 150. The valves can be either manual or automatic. In other words, the valve may be manually operated by the user/technician or can be automatically operated, for example, by a controller, when a particular condition is met (e.g., the return line valve 281 closing when air is detected in the line 140, as discussed below).

It should also be noted that any or all of the above described lines can include an air detector to detect the presence of air within the line. For example, the return line 140 may contain an air detector 250. The presence of air bubbles within the lines can be problematic for the operation the system and may also be harmful to the subject if the air bubbles enter the blood stream. Therefore, the air detector 250 may be connected to an interlock that stops the flow within the return line 140 in the event that an air bubble is detected (e.g., by stopping the return pump 142 or closing the valve 281 on the return line 140), thereby preventing the air bubbles from entering the subject. Additionally, in some embodiments, the return line 140 may also include an air trap 270. The air trap 270 may be used to remove any air from the fluid (e.g., blood components or compensation fluid) that is being returned to the subject.

Additionally, as shown in FIGS. 3 and 4, the blood component separation device 150 may include a line sensor 260 located near the outlet port PT2. The line sensor 260 may be an optical sensor that includes an LED that emits light through the fluid passing through the outlet port PT2 and the sensor 260. A photo detector located opposite the LED light (e.g., on the opposing side of the fluid) receives the light that passes through the fluid and can determine the density of the fluid passing based on the amount of light received. Based on this calculated density, the line sensor 260 can determine the type of component that is passing through the sensor (e.g., platelets or plasma). In some embodiments, the line sensor 260 may be connected to one or more of the valves discussed above, and may control the operation of the valve (e.g., either directly or through a controller). For example, if the line sensor 260 detects a change in density indicating that the flow through the sensor is changing from plasma to platelets, the line sensor 260 may close the valve heading to the plasma bag 158 and open the valve to the platelet bag 156.

The system may also include a recirculation pump 210 that recirculates fluid within the system and withdraws blood components from the blood component separation device 150. For example, the recirculation pump 210 can be used to remove the plasma from the blood component separation device 150 or send compensation fluid from the compensation fluid source 230 to the blood component separation device 150 during surge elutriation, which is discussed in greater detail below.

Figure 5:
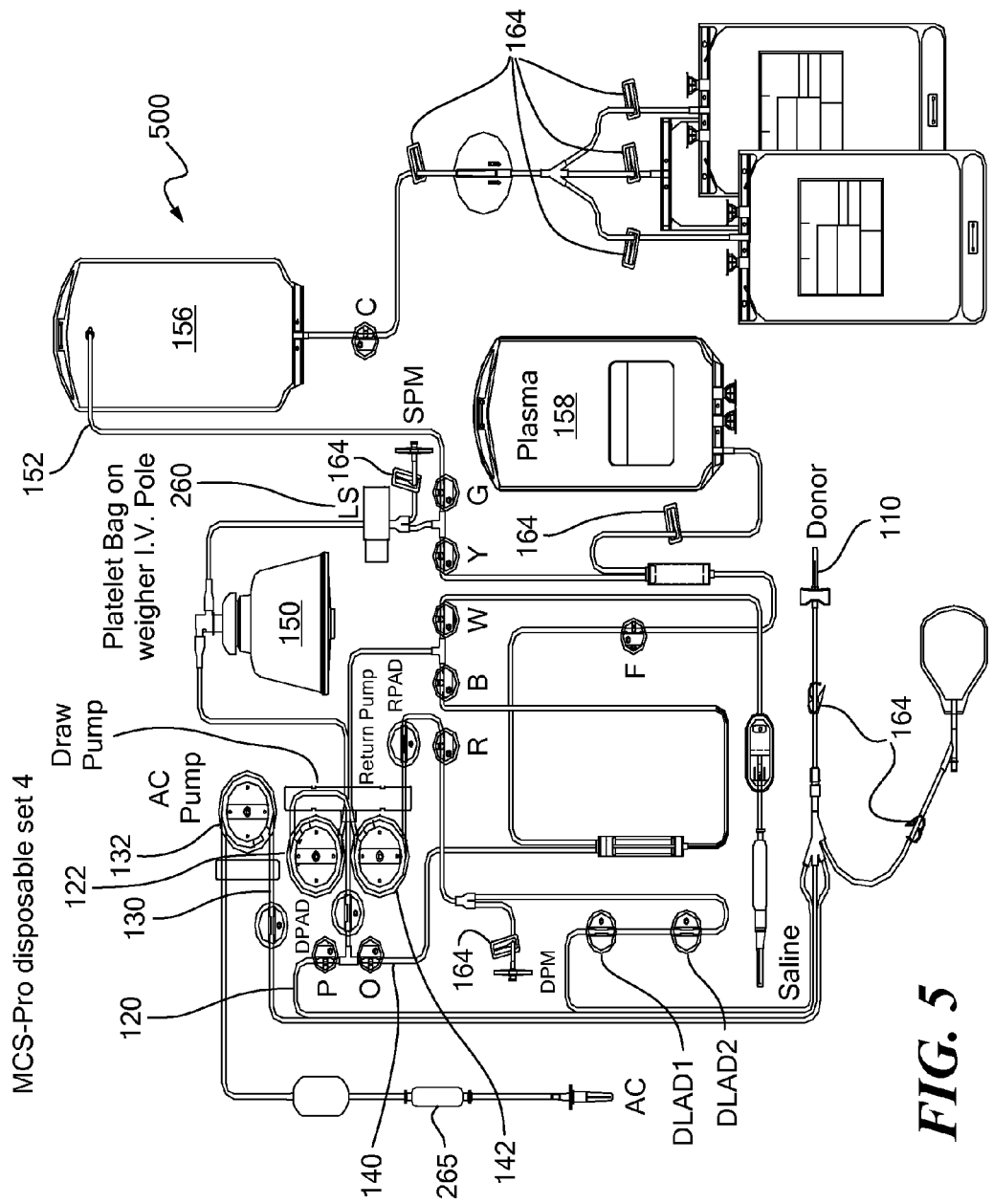
FIG. 5 shows an embodiment of a disposable set containing components from the apheresis system shown in FIGS. 2, 3, and 4, in accordance with embodiments of the present invention.

As shown in FIG. 5, the above described system and corresponding components can be packaged together as a disposable set 500. The disposable set 500 can include some or all of the disposable components required for blood processing. For example, the disposable set may include, among other things, the draw line 120, the return line 140, the anticoagulant line 130, all other system tubing, a number of valves 164 to stop the flow within a given line, the platelet bag 156, the plasma bag 158, the anticoagulant filter 265, and the venous access device 110. Therefore, when a user/technician is about to perform a blood apheresis process, they need only open the pre-packaged disposable set and install the components in the appropriate apheresis machine. Additionally, when the apheresis process is complete, the user/technician need only remove the disposable components and dispose of them appropriately.

Figure 6:
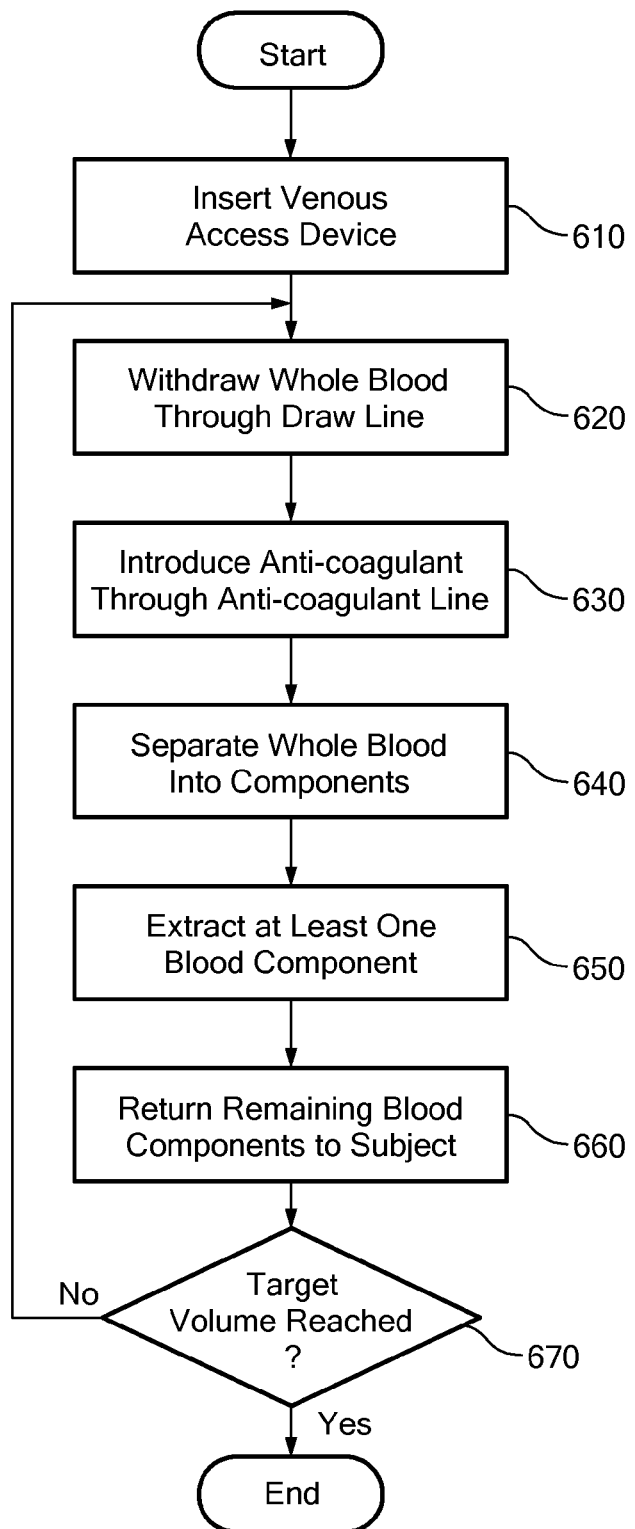
FIG. 6 shows a flowchart showing the steps of one method of using the three-line, single access system in accordance with one embodiment of the present invention.

FIG. 6 schematically shows a flowchart depicting a method for using the three-line, single access apheresis system described above. In particular, the method first inserts the venous access device 110 into the subject (Step 610), and then begins to withdraw whole blood through the draw line 120 (Step 620). As mentioned above, the direction, rate, and duration of the flow within the withdraw line 120 is controlled by the draw pump 122. As the whole blood is withdrawn from the subject, the anticoagulant pump 132 introduces anticoagulant from the anticoagulant source 134 into the whole blood via the anticoagulant line 130 (Step 630). As described above, the anticoagulant prevents the whole blood from coagulating within the system.

Once the anticoagulated whole blood reaches the blood component separation device 150, the blood component separation device separates the blood into the constituent components (e.g., red blood cells, plasma, platelets, and white blood cells) in the layered orientation described above (Step 640). The technician operating the system may then extract one or more of the components (the component extracted is dependent on the purpose of the procedure) (Step 650) and return the remaining blood components to the subject (Step 660). As discussed above, the returned components are returned to the subject via the return line 140 and return pump 142. During the return process, the withdraw line 120 and draw pump 122 can be isolated from the donor (and the return line 140) by closing valve 280 located on the draw line 120. Additionally, during the return process, the anticoagulant pump 132 may be stopped to prevent the flow of anticoagulant. If the target volume of components is harvested/collected (Step 670), the procedure is complete. Otherwise, the system may be used to harvest/collect a second batch of components by repeating steps 620 through 660.

Figure 7:
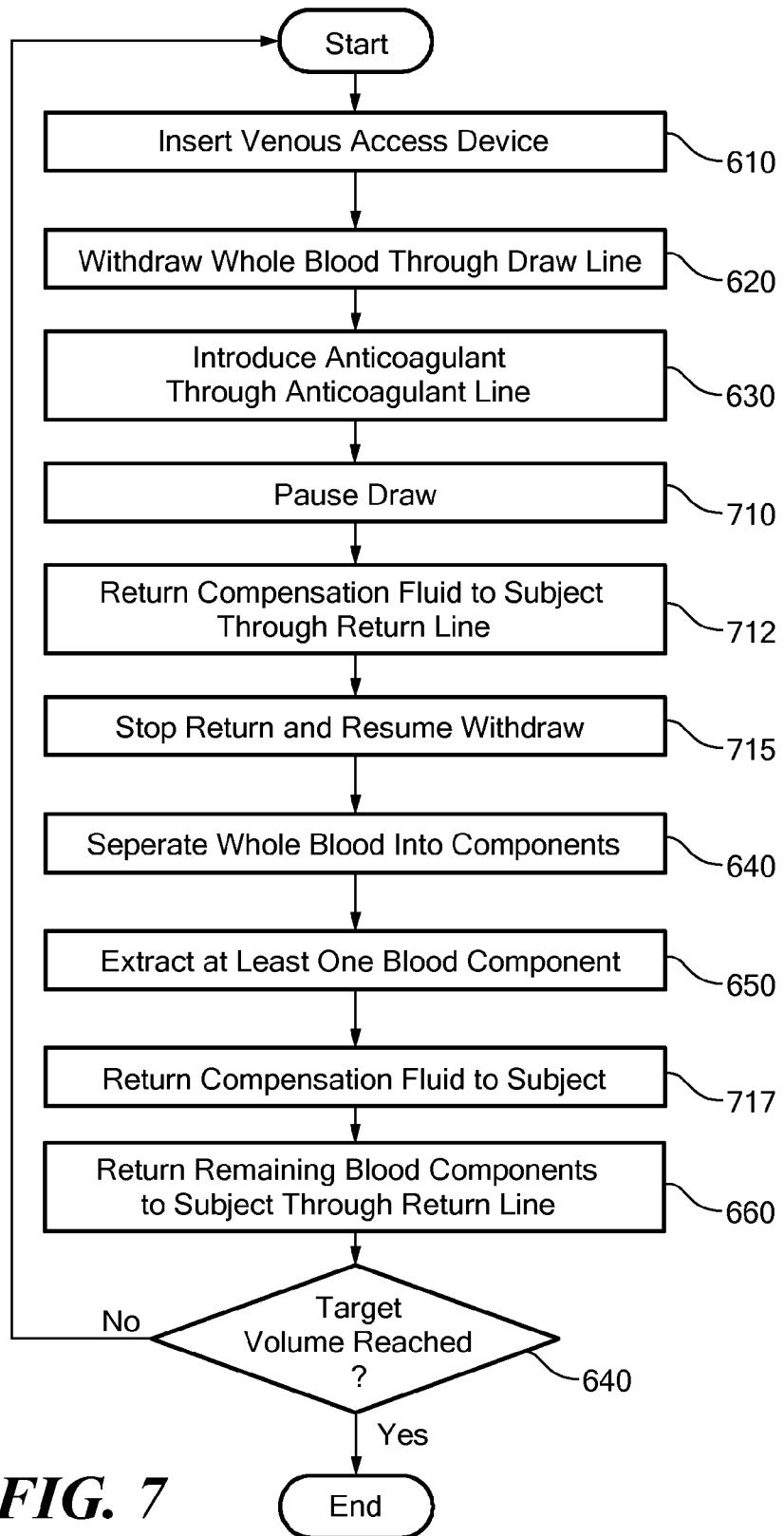
FIG. 7 shows a flowchart showing the steps of a second method of using the three-line, single access system in accordance with an additional embodiment of the present invention.

In accordance with other embodiments, and as shown in FIG. 7, the method of using the three-line, single access apheresis may also include several additional, optional steps. In particular, after withdrawing a volume of whole blood through the draw line (Step 620) and introducing anticoagulant (Step 630), the method may pause the withdrawal (Step 710) and return compensation fluid to the subject (Step 712). The compensation fluid can be returned to the subject via the return line 140 and return pump 142, so that the downtime required to switch between the withdrawal step and the return step is greatly reduced. The amount of compensation fluid returned to the subject can be substantially similar to the volume of whole blood withdrawn from the patient or it can be based on the calculated volume of blood components to be removed (e.g., the amount of plasma to be removed). After the appropriate amount of compensation fluid is returned to the subject, the method may then stop the return and resume the withdrawal of whole blood (Step 715), for example, until a pre-defined volume of red blood cells is sequestered in the blood component separation device. By returning the compensation fluid to the subject in this manner (e.g., pausing the draw step to return compensation fluid), the extra corporeal volume at any given time may be reduced and the subject's tolerance to the procedure is increased.

It should be noted that the volume of whole blood withdrawn from the subject does not need to equal the volume of the blood component separation device 150. In some embodiments, the volume of withdrawn blood can be less than that of the blood component separation device 150 such that air is still present in the separation device 150. In such embodiments, the subject may have a higher tolerance to the procedure because of the lower extra corporeal volume. Additionally, as discussed above, embodiments of the present invention may pause the draw step when the blood component separation device still contains air (e.g., when the blood component separation device 150 is not full), return compensation fluid to the subject, and then resume the draw to fill the remaining volume within the blood component separation device volume. Again, this minimizes the amount of extra corporeal volume and improves the subjects tolerance to the procedure.

The blood component separation device can then separate the anticoagulated whole blood into the constituent components (Step 640), and one or more of the components may be extracted (Step 650), as discussed above. During this time, the method may, once again, return compensation fluid to the patient (Step 717). Additionally or alternatively, if the components are to be extracted via surge elutriation, the technician may begin to send compensation fluid to the blood component separation device 150. The compensation fluid displaces plasma within the separation device to either the plasma bag 158 or a waste bag 220 (FIG. 3). The method may continue this surge step until a known percentage of plasma is displaced from the separation device 150 (e.g., 85%). The method may then stop the blood component separation device 150, and return the contents of the separation device (e.g., the remaining blood components and the compensation fluid) to the subject via the return line 140 (Step 660). As mentioned above with respect to FIG. 6, if the target volume of components (e.g., plasma) is harvested/collected (Step 670), the procedure is complete. Otherwise, the system may be used to harvest/collect a second batch of components by repeating steps 620 through 660.

Some embodiments of the present invention may also include one or more pressure sensors on the return line 140. The pressure sensors (not shown) measure the pressure within the return line 140. The measured pressure may then be used to determine a subject access pressure that corresponds to the pressure at the point of access with the subject. Embodiments of the present invention may then control the flow within the return line 140 based on the subject access pressure. For instance, if the subject access pressure is to high, the return pump 142 can reduce the flow within the return line 140 in order to reduce the subject access pressure and avoid harm to the subject.

Once the system returns the remaining blood components and compensation fluid to the subject, some embodiments of the present invention can determine the amount of blood component (e.g., plasma) extracted and the amount replaced with compensation fluid. In such embodiments, the system may first calculate the bowl mean hematocrit and plasma exchange percentage. The system may then use this information to determine the amount of plasma extracted and the amount of plasma replaced with compensation fluid.

It should be noted that all of the components of the system should be made of suitable materials that are compatible with the substance with which they are in contact. For example, the draw line 120, the return line 140, and lines 152 and 154 should be compatible with blood and blood components. Additionally, the platelet bag 156 and the plasma bag 158 should be compatible with platelets and plasma, respectively. Likewise, the anticoagulant line 130 should be compatible with anticoagulant.

It should be noted that the size and capacity of all of the pumps within the above described embodiments need not be identical. For example, the draw pump 122 may be larger and have a greater capacity than the return pump 142 and the anticoagulant pump 132. Additionally, the flow rates through the respective lines need not be equal. For example, in some embodiments, the flowrate through the withdraw line 120 and draw pump 122 may be greater than the sum of the flowrates through the return pump 142 and the anticoagulant pump 132.

It is important to note that any of the above described embodiments may be used for a variety of apheresis and blood processing procedures. For example, embodiments may be used for red blood cell apheresis, plasma apheresis, platelet apheresis, or a variety of therapeutic applications.

Although the above discussion discloses various exemplary embodiments of the invention, it should be apparent that those skilled in the art can make various modifications that will achieve some of the advantages of the invention without departing from the true scope of the invention.

We claim:

1. A method of collecting and exchanging blood components comprising:
   (a) inserting a venous-access device into a subject, the venous-access device connected to a draw line, an anticoagulation line, and a return line;
   (b) withdrawing blood from the subject through the draw line, the draw line connected to a blood component separation device, the flow through the draw line being controlled by a draw line pump, the blood component separation device having an inlet and an outlet;
   (c) introducing anticoagulant into the withdrawn blood through the anticoagulant line, the flow through the anticoagulant line being controlled by an anticoagulant line pump;

(d) separating the withdrawn blood into a first blood component and a second blood component using the blood component separation device;
(e) extracting the first blood component from the blood component separation device;
(f) returning the second blood component to the patient through the return line, the flow through the return line being controlled by a return line pump, wherein the return line fluidly connects to the inlet of the blood component separation device and the venous-access device, the return line fluidly connecting to the venous-access device at a point between the draw line pump and the venous-access device.

2. A method according to claim 1, wherein the blood component separation device is a centrifuge bowl.

3. A method according to claim 1 wherein extracting the first blood component from the blood component separation device includes introducing compensation fluid into the blood component separation device and extracting the first blood component by surge elutriation.

4. A method according to claim 1, wherein the amount of blood withdrawn from the subject does not fill the blood component separation device.

5. A method according to claim 1 further comprising:
(g) pausing the withdrawal of blood while returning the second component to the subject.

6. A method according to claim 5 further comprising repeating steps (a) through (g) until a target first blood component volume is extracted.

7. A method according to claim 1, further comprising:
monitoring a pressure within the return line; and
adjusting the flow of fluid within the return line based on the monitored pressure to maintain the pressure within a desired pressure range.

8. A method according to claim 1 further comprising returning a volume of compensation fluid to the subject after a volume of blood is drawn from the subject.

9. A method according to claim 1 further comprising:
(g) pausing the withdrawal of blood prior to filling the blood component separation device;
(h) returning a volume of compensation fluid to the subject; and
(i) resuming the withdrawal of blood from the subject.

10. A method according to claim 9, wherein the volume of compensation fluid is a function of a volume of first blood component extracted from the blood component separation device.

11. A method according to claim 10, wherein the compensation fluid is returned to the subject via a compensation fluid line, the compensation fluid line connected to a compensation fluid source and fluidly connected to the return line.

12. A method according to claim 1, wherein the return line is a dedicated return line.

13. A method according to claim 1, wherein extracting the first blood component from the blood component separation device includes transferring the first blood component to a first blood component bag.

14. A method according to claim 13, further comprising:
reintroducing the first blood component from the first blood component bag into the blood component separation device via a dilution/extraction line, the dilution/extraction line fluidly connected to the first blood component bag and the blood component separation device.

15. A method according to claim 1, wherein the blood component separation device is a two port centrifuge bowl.

* * * * *